(12) United States Patent
Mahan

(10) Patent No.: US 8,440,009 B2
(45) Date of Patent: May 14, 2013

(54) CLADOPHORA BASED MATERIALS AND METHOD OF MAKING SAME

(75) Inventor: Wesley A. Mahan, Geneva on the Lake, OH (US)

(73) Assignee: Green Wave Innovative Solutions, LLC, Cape Coral, FL (US)

( * ) Notice: Subject to any disclaimer, the term of this patent is extended or adjusted under 35 U.S.C. 154(b) by 476 days.

(21) Appl. No.: 12/766,550

(22) Filed: Apr. 23, 2010

(65) Prior Publication Data

US 2010/0297436 A1  Nov. 25, 2010

Related U.S. Application Data

(60) Provisional application No. 61/172,014, filed on Apr. 23, 2009.

(51) Int. Cl.
*C09D 5/18* (2006.01)
*C09K 21/06* (2006.01)
*A62C 3/00* (2006.01)

(52) U.S. Cl.
USPC .............. 106/18.11; 106/18.13; 252/601; 424/195.17; 428/920; 428/921

(58) Field of Classification Search .............. 106/18.11, 106/18.13; 252/601; 424/195.17; 428/920, 428/921
See application file for complete search history.

(56) References Cited

U.S. PATENT DOCUMENTS

| 4,235,043 A | 11/1980 | Harasawa |
| 5,753,570 A | 5/1998 | Garrigus |
| 5,779,960 A * | 7/1998 | Berlowitz-Tarrant et al. .......... 264/176.1 |
| 6,136,329 A | 10/2000 | Boratyn |
| 7,080,478 B2 | 7/2006 | Levy |
| 7,087,105 B1 | 8/2006 | Chappell |
| 7,479,167 B2 | 1/2009 | Markels, Jr. |
| 7,691,388 B2 * | 4/2010 | Ewart et al. .............. 424/195.17 |
| 2007/0184088 A1 | 8/2007 | Jung |
| 2011/0307976 A1 * | 12/2011 | Ploechinger .................. 800/296 |

FOREIGN PATENT DOCUMENTS

WO    WO2007092359 A2    8/2007

* cited by examiner

*Primary Examiner* — Anthony J Green
(74) *Attorney, Agent, or Firm* — George W. Moxon, II; Brian P. Harrod

(57) ABSTRACT

A process for manufacturing fire resistant materials comprising the steps of recovering Cladophora algae; mixing said algae with water to form an aqueous mixture; mixing a chlorine based solution to the mixture to kill the algae and any bacteria and to form an algae-based product; allowing the algae-based product to separate and rise to the surface of the aqueous mixture; skimming the algae-based product from the surface of the mixture; drying said recovered algae-based product; and recovering the dried algae-based product.

14 Claims, No Drawings

CLADOPHORA BASED MATERIALS AND METHOD OF MAKING SAME

CROSS REFERENCE TO RELATED APPLICATIONS

This application claims the benefit of provisional application Ser. No. 61/172,014, filed Apr. 23, 2009, which is entitled FIRE RETARDANT MATERIALS, SYSTEMS AND METHODS and is incorporated herein by reference.

TECHNICAL FIELD

The invention relates to a process for forming compositions from Cladophora algae compositions, for use in, for example, fire retardant and insulating compositions formulated from the recovered Cladophora algae based compositions.

BACKGROUND OF THE INVENTION

Fires result in significant losses of life and property each year, and have a great impact and cost on society. To combat fire related losses, fire retardant materials have been developed, such as chemicals that can be applied to a combustible object to reduce flammability or retard the spread of fire over its surface. Such materials are commonly applied to textiles and building materials where fire resistance is particularly desirable. Many fire retardants are synthetic phosphorus-containing compounds for example, but such chemicals can create other problems concerning health and safety due to toxicity issues for example. Therefore, there remains a need for improved non-toxic fire retardant compositions that can be applied to or incorporated into building materials, textiles, and other objects and materials where fire resistance is desirable.

It would be desirable to provide fire retardant materials that could be used in a variety of manners and in or with a variety of products to impart fire retarding or flame resistant/fire retardant characteristics and attributes. For example, it may be desirable to protect building structures from wildfires, and the use of fire retarding construction materials may provide some protection. But due to the nature of the fires, which can burn very hot, even use of such materials may not be sufficient to protect a structure. It may be desirable to provide the ability to coat a structure with a fire retardant material in a fire emergency to enhance protection of the structure. Building materials incorporating or formed of the fire retardant materials could also provide protection. It would also be desirable to allow non-toxic fire retardant materials to be used in textile articles or other materials to provide desired fire retardant characteristics to the articles or products made therefrom, such as clothing, carpet, or many other products. It may also be desirable to provide a fire retardant material that can be incorporated into other products or materials to add flame or fire resistance. There is an ongoing need to improve the flame retardant materials to impart flame-retardant attributes while being non-toxic and easily produced. It is also desirable to provide fire retardant materials wherein the materials are halogen-free to reduce smoke and toxicity.

Algae are plantlike protists, which are eukaryotic, unicellular or multicellular organisms. Like plants, algae have chloroplasts, and their cells are strengthened by a cell wall. Algae refer to aquatic organisms that carry on photosynthesis, and are typically part of a fresh water system's phytoplankton. Algae may be classified according to its color, which come in a variety of color such as green Chlorophyta, brown Phaeaphyta, golden brown Chrysphyta, and red Rhodophyta. Cladophora is a green algae, and is comprised of filaments that are branched, and often spaced from one another. Fronds are the whole system of branched filaments and are generally attached to materials or a substrate. Fronds of Cladophora are frequently covered with epiphytic diatoms in a natural environment, and in the present invention, such materials are generally removed in a refining process as will be described. When growth conditions are favorable, Cladophora reproduces asexually. The adult alga divides, forming zoospores or flagellated spores that are smaller than the parent cell. A spore is a haploid body that develops into a mature adult. When growth conditions are unfavorable, Cladophora reproduces sexually. Gametes from two different mating gametes come into contact and join to form a zygote. When a zygospore germinates, it produces four zoospore by meiosis. A heavy wall forms around the zygote and it becomes a resistant zygospore, which is able to survive until conditions are favorable for germination. The zoospores are haploid and when released, grow into adult algal filaments. Isogamy is the condition where gametes are identical. These gametes are known as isogametes.

Cladophora algae occur naturally in fresh water, such as ponds or the Great Lakes, where the algae can be produced in mass, and in the presence of fertilizers that promote growth in such water environments, the algae can be a serious problem. Their removal and consumption can be a positive for the environments. Alternatively, were the algae are not naturally available, they can be produced in interior environments using tanks or the like with grow lights that promote plant growth by emitting an electromagnetic spectrum appropriate for photosynthesis. The emitted light spectrum may be similar to that from the sun, allowing indoor growth with outdoor conditions. It is known that natural daylight has a high color temperature (approx. 6000 K) and appears bluish, and through the use of the color rendering index, lighting systems have been developed to match the natural color of regular sunlight. Factors that can be controlled to facilitate growth of the algae are light, temperature, the chemical composition and acidity or alkalinity of the water. For high production, the water environment is exposed to sunlight (natural or artificial) to allow for photosynthesis, with the Cladophora grown in a shallow water environment. In a tank or the like, walls may be made of glass or plastic to allow light into lower portions thereof to promote growth in all areas of the tank. The temperature of the water should be maintained warm, such as in the range of 50-80 degrees F. for example, and the water conditioned with inorganic compounds, such as nitrogen and phosphorous, other nitrates and carbon dioxide, to promote the growth of the Cladophora algae. In this manner, sufficient quantities of Cladophora may be produced for desired applications.

SUMMARY OF THE DISCLOSURE

The invention relates to fire retardant compositions and methods of making such compositions, and products using and methods of use of such compositions. The composition comprises a material produced from Cladophora algae, wherein the material is formed from refined Cladophora algae. The material may be formed into fibrous material or powdered, and combined with other materials and possible additives based on the application thereof. The powdered algae-based product may be used itself in forming a fire retardant composition or incorporated into textile materials, into non-halogenated flame retardant compounds manufactured from a variety of thermoplastic resins, including polyamide/nylon (PA), polycarbonate (PC), and polycarbonate/ABS (PC/ABS) blends. The material may be used to form a coating for application to a structure for providing fire resistance to the structure, as building products such as panels, or blown in insulation type materials, or as an additive to paints or the like, or in various other applications and examples.

The invention also relates to a process for manufacturing fire resistant materials comprising the steps of recovering Cladophora algae; mixing said algae with water to form an aqueous mixture; mixing a chlorine based solution to the mixture to kill the algae and any bacteria and to form an algae-based product; allowing the algae-based product to separate and rise to the surface of the aqueous mixture; skimming the algae-based product from the surface of the mixture; drying said recovered algae-based product; and recovering the dried algae-based product.

The present invention relates to fire retardant materials used for protecting building structures either by coating thereof with the material or use in building materials used to make the structure, as well as textile articles, for example, fibers, filaments, yarns and fabric structures having the materials incorporated therein, wire sheathing formed from such material, paper materials formed therewith, and other materials which exhibit flame-retardant properties.

In another aspect, this invention provides a method of using a fire retardant composition by providing an amount of Cladophora algae which has been dried, refined and processed into a powderized material; adding the powderized material to a liquid base to form a liquid coating material; applying the liquid coating material to a structure in a predetermined thickness before the structure may be exposed to fire; and, optionally, removing the coating from the structure after the risk of exposure to fire has passed.

These and other aspects and advantages will become more apparent after careful consideration is given to the following description of various examples of the invention.

DETAILED DESCRIPTION OF THE INVENTION

The invention provides fire retardant compositions and products comprising refined Cladophora algae-based compositions. The compositions may be in any form that allows for effective application and use, such as liquids, gels, pastes, foams, particles, fibers, extrusions and other suitable forms. The fire retardant compositions may be applied by methods known to those skilled in the art. "Flame or fire retardant" means that the initiation and/or spread of flame or smoke slowed or prevented entirely by inhibiting the combustion reaction in the flame.

A process for manufacturing a materials, based upon the Cladophora algae, for use as, e.g., fire resistant materials includes the steps of recovering Cladophora algae; mixing the algae with water to form a mixture; adding a chlorine based solution to the mixture to kill the algae and any bacteria to form an algae product; skimming the algae product from the surface of the mixture to get a wet algae product; drying said recovered product; and recovering the dried algae product.

In its natural state, Cladophora may have various other materials associated therewith, such as contaminants like diatoms that attach to the algae fronds, and other organic or inorganic materials for example. The Cladophora algae is harvested by cutting or other suitable method, at a point above its attachment to a substrate, to allow continued growth from the remaining portion of the fronds. In general, the algae grow on substrates or surfaces in a natural environment, such as rocks, and in a controlled environment, a suitable substrate can be provided in the water for facilitating growth therefrom.

For example, a mesh substrate may be provided onto which the algae may attach and be grown, which mesh substrate facilitates the flow of water around the algae and the introduction of nutrients thereto. For harvesting, the substrates could be easily removed and a length of algae cut therefrom, while leaving a portion attached to the substrate, which can then be reintroduced into the water for continued growth. Alternatively, the algae could be harvested with the substrate in place. Upon harvesting, the algae may then be cleaned, to remove any contaminants at 16. Depending on the nature of possible contaminants, the process of cleaning the harvested algae can vary. For example, the algae may be subjected to chlorine, or other suitable materials to disinfect or kill and remove any other organisms and/or organic materials that may be found in association with the algae. Algaecides may also be usable for example, as they would tend to kill other organisms and/or organic materials also. Other methods, such as the use of oxygen to kill bacteria, high concentrations of carbon dioxide, or other methods of cleaning to make it halogen free. Other techniques such as subjecting the material to ultraviolet light or even ultrasound may be possible. The cleaning step is also designed to effectively kill the Cladophora algae and produces an algal residue. If other materials are present, they can be removed by any suitable techniques, such as filtering or the like. If a cleaning compound is used that leaves any residue, this may be rinsed if desired. Possible methods for sorting the algae away from other materials may include industrial centrifugation, hydro or air based separation, or other suitable techniques. It may also be possible to heat the material to burn off the contaminating matter.

As an example, Cladophora can be collected by skimming the material off the top of the water in Lake Erie close to shore and put into a large bucket with holes to drain off excess weight from water. The material is further rinsed with a spray assembly to remove any foreign substances (such as shells, small rocks etc). The Cladophora collected on the shores of the lake is a dead or almost dead algae that is covered by diatoms which are mono-cellular algae with an inorganic porous shell (mainly constituted of silica). It is important to note that when Cladophora is collected it desirable that it be significantly or almost completely covered with diatoms. The Cladophora/diatom system can be harvested either naturally and/or cultured "artificially" from cultured algae pools. In the case of cultivated Cladophora, it will be necessary to introduce diatoms into the pools so that it will grow on the Cladophora.

In a 40 gallon plastic container, a 5 gallon bucket full of Cladophora was added. 10 gallons of faucet water and a ½ gallon of weak solution of 6% Sodium Hypochlorite was added containing no phosphorus. The combined solution was stirred for 3 minutes and let to rest for 1 hour at which time the Cladophora transformed from green to a brown color and foaming occurred. The algae-based composition arose to the top of the plastic container and the solution formed 2 layers. The top layer with the brown material was decanted off and saved for further processing. The purified wet treated material was put in a large flat tray with small holes in it for drying and compression by another flat tray with weight on it was placed over the top and left over night. The flat tray was removed the next day and sample was placed in the sun to dry.

After chemical treatment of the algae-based composition, a 3 dimensional structure of diatoms supported by cellulose was obtained. The chlorophyll has been removed from the cellulose fibers of the alga and that only the cellulose film remains from the alga in the 3 dimensional structures. The diatoms present on the Cladophora prior to the chemical treatment remain attached to the cellulose films or fibers. Hence, the diatoms form a continuous 3 dimensional structure.

Although in the example above chlorine was used to kill the Cladophora and remove any part that was not cellulose or diatoms, many other chemical products can be used to reach a similar result. For example one can use different type of acids, alcohols, aldehydes, and the like and/or a mixture of these solvents to reach similar results and yield a 3 dimensional and self standing structure of diatoms. Gas treatment such as carbon dioxide, ozone can also yield similar results. Another example of treatment to kill the alga is UV exposure, or other optical treatment that would kill the living part of the Cladophora without damaging the structure. A combination of 2 or more processes can be used as well to yield different results in the removal of the living components of the algae but yet resulting in a similar 3 dimensional structure in which diatoms are forming the scaffold of the 3 dimensional structures.

Any concentration, flow rate, temperature of reaction, light intensity can be used as long as the structure of the material is not compromise and that the end product is a 3 dimensional structure with good mechanical properties of self standing diatom porous scaffold. Chlorine concentration as little as 1% by volume in water and as concentrated as chemically feasible can be used, the completion of the reaction to yield an acceptable product with no living algae will strongly depend on the concentration used.

As mentioned above, diatoms or diatomaceous earth have been used as fillers for many applications. Similarly purified diatoms have been used for various applications (especially biomedical and filters). Hence we claim that the newly processing method described above applied to the Cladophora/diatom system yields a unique structure and a unique material that can be used for any of the applications in which diatoms are already being used as fillers or in the purified form. The uniqueness of the discovery here afore mentioned is that the treated Cladophora/diatoms constitute the bulk of the material and do not require any supporting structure.

An example of application that has been tested is the fire proof properties of the self standing structure. Diatoms are commonly used as fillers to reinforce fire proof properties of building materials. However diatoms as fillers do not prevent from the bulk of the building material to catch fire or to emit toxic fumes.

A flame coming out of a propane torch (Temperature >3000° F.) was directly applied onto a panel of the self standing structure (¼ inch thick) of the chlorine treated Cladophora/diatom system for at least 5 minutes. The panel did not catch fire, did not emit any fume or any odor indicating of combustion. The temperature on the side of the panel that was not exposed to the flame remained approximately close to the room temperature and could be touched with bare hands without any physical consequences or discomfort.

The 3 dimensional structure produced by the present invention on a Cladophora/diatom system can also be used in combination with other materials that are commonly used for fabricating commonly used shapes and applications.

After the purified material was dried it was fed into a machine to chop and grind the material into finer particles, the bagged material was then ready for the next processing steps.

The bagged material was reconstituted back into a solution of $H_2O$ and an anti fungicidal and mold inhibitor was added orthoboric acid 99.00% active ingredients followed by commercial grade type S cement ASTM C-91 and non flammable polyvinyl acetate latex binder. The cement and latex had been added for ridged applications such as insulation and the like, but cement or latex is not needed for most other uses like application for prevention of homes from forest fires and the like. Other binders and additives can be added depending upon the performance desired. For example, three-dimensional shapes such as boards, papers, and objects can be made by combing the algae-based composition with binders such as polymeric materials or compositions, with corn starch to make paper or paper-like objects, or with cement or latex binders, as noted above.

The procedure for making a ridged three dimensional object sample involved the following:

12 cups the algae-based composition of the present invention 7 cups $H_2O$ 4 cups Type S ASTM C-91 Cement 1 cup Boric Acid ⅓ cup white Non-flammable polyvinyl acetate latex binder (Glue)

The contents $H_2O$, Cement, Boric acid, ⅓ polyvinyl acetate latex binder were mixed together and poured over the Algae-based composition. The mix was stirred thoroughly and poured into another flat plastic tray and dried by room temperature overnight. Then taken out of tray and placed on a rack. Drying was accelerated by using heaters, sunlight, and the like.

This material was obviously much lighter than regular cement and tougher in flexion. A panel of this blend material was tested for flame resistance in the same conditions as the single panel of chlorine treated algae-based composition/diatoms system (described previously) and the composite was not flammable, did not emit any fume.

The algal residue is then dried at to form a fibrous material extract. The fibrous material extract may then be used in producing fire retardant materials. Optionally, the fibrous material may be further processed at for transforming the fibrous material into another form for producing fire retardant materials or introducing the materials into products to provide fire retardant characteristics, such as for example a powderized form. If desired, adding the extract to a diluents to obtain a fire retardant composition may be performed. The fire retardant materials are non-halogenated as desired. As will be hereinafter described, such a powder may then be used to impart fire retarding characteristics to different products or coatings. The powder may comprise particles, which may mean granules, fibers, flakes, spheres, platelets, and/or other solid shapes and forms known to those skilled in the art. Different particle sizes or mesh sizes may be formed for different applications, such as by screening or other separation methods. As merely an example, the particle sizes useful for various applications may be in the range of 1 micron to inches, but any suitable size is contemplated.

In producing the algae-based compositions of the present invention, the algae may have or contain organisms trapped in the alga materials, and the step of cleaning may further include the step of removing detritus from the algal materials, which can be done by suitable sorting techniques, such as by drying and mechanically sifting or filtering out extraneous materials from the fibrous algal materials, or any other suitable method. Thereafter, the step of subjecting the algal material to chlorine or the like to kill organisms that may remain can be carried out and the remaining steps performed as described. As the presence of Cladophora on shores of lakes or rivers presents aesthetic and odor problems that impairs recreational or other uses of such environments, the ability to remove and effectively use such materials may be of significant advantage. For example, in the Great Lakes in the Unites States, recurring algae blooms lead to unsightly and foulsmelling beaches and have negative economic consequences as a result of the lowered beach use. In addition, Cladophora blooms result in reduced quality of drinking water and decreased property values. There has been a resurgence of algae blooms, possibly caused by increased nutrient inputs, increased water clarity, increased water temperature and/or changing lake level. The Cladophora could be harvested from the lakes themselves or gathered from beaches once it washes onto the beaches, to mitigate these negative factors. In the event large mats of Cladophora wash ashore, they typically carry with them large numbers of zebra mussels, small crustaceans or other organisms that shelter in the algae. The organisms contribute to the odor as they decompose and/or become food for waterfowl. The higher concentration of birds also results in fecal material being deposited on the algae. The organisms and fecal matter, or other contaminants are removed in the refining process according to the invention.

The fire retardant material may be formed as a slurry for application to a structure, such as by mixing a powderized material as previously describe with water or another liquid. If desired, a binding material could be mixed with the powdered algae-based composition to provide desired characteristics relating to adherence or drying of the materials once they are applied. The slurry material may then be conveyed through a hose and pneumatically projected at high velocity onto a surface of the structure. The slurry may be formed to allow placement and compaction at the same time due to the force with which it is projected from the nozzle of hose. It can be impacted onto any type or shape of surface, including vertical or overhead areas. Alternatively to a slurry, the system may also be used in a method of blowing dry material out of hose with compressed air, and wetting it as it is released. Suitable machines for such as purpose may be similar to those referred to as "gunite" or "shotcrete" type of machines. The dry mix method involves placing the dry ingredients into a hopper provided on the vehicle and then conveying them pneumatically through a hose to the nozzle. A nozzleman controls the addition of water at the nozzle. The water and the dry mixture may not be completely mixed, but is completed as the mixture hits the receiving surface. Using a dry mix process, the water content can be adjusted instantaneously by the nozzleman, allowing more effective placement in overhead and vertical applications without using accelerators. Wet-mix application involves pumping of a previously prepared fire retardant slurry to the nozzle. Compressed air is introduced at the nozzle to impel the mixture onto the receiving surface. The wet-gun procedure generally produces less rebound, waste (when material falls to the floor), and dust compared to the dry-mix procedure. The wet-mix process may allow larger volumes of materials to be placed in less time. The system could also use a rotary gun, with an open hopper that can be fed continuously. The nozzle may be controlled by hand on smaller structures for example, or held by mechanical arms and operated by a hand-held remote control for example. Any other suitable arrangement for spray application of the fire retardant materials onto the surface of the structure may be used, such as a small portable unit that a homeowner could use for example. As a further example, the system could be deployed on fire engines for use in protecting portions of a structure that have not yet been exposed to fire, or protection of adjacent structures to a fire in progress. Such systems could also be used by fire departments or others to protect structures that may be exposed to wild fires, or the owners of structures could employ systems to protect structures in such an event.

The system of the invention may be adapted and useful for protecting a myriad of structures, including housing, industrial buildings, warehouses, and any other structures. In the event of a risk the structure may be exposed to fire, the system (or like system) may be used to spray the fire retardant mixture on the entire outer surface of the structure, including the roof and all of the walls, in order to form an outer coating or shell over the exterior of structure. The material adheres to the exterior temporarily while risk of exposure to fire exists, and once such risk has passed, the material may simply be washed off the structure. As the fire retardant material is non-toxic, it will not harm the environment upon being washed from the structure. In this example, the provision of a vehicle which can apply the material enables the truck to simply drive up to the building site, which is an easy and convenient way of applying the material. The fire retardant material and any additives can be mixed at the site by the truck apparatus, and then pumped through hose to nozzle where compressed air is applied to the flowing stream of material through hose for applying the material to structure. Merely as an example, the materials may be pumped through a hydraulic pump to produce a stream of material in the hose at a desired pressure, such as a pressure of 75 lbs. per square inch maintained in a 1 inch diameter hose, for example. Compressed air is pumped through the hose at a desired pressure, such as 75-165 lbs. per square inch, so that the mixture is sprayed as aerated slurry onto the outer surface of the structure. The sprayed material adheres to the outer surface of the structure and can be applied in layers by passing the nozzle back and forth across the surfaces, or in greater thickness in a single pass. The truck can be used to mix and apply the fire retardant material coating, and may carry the mixing and spraying equipment. The truck may have a lifting system (not shown) to lift the dry algae materials into a hopper for mixing, and/or to support the nozzle at a desired location. The truck may also include a tank for holding the liquid slurry, and for water for mixing. Hydraulic pumps may be used to connect all of the tanks to a mixing chamber, so that metered amounts of each of the materials are conveyed into the mixing chamber in order to form a fire retardant mix. A mixing blade may be provided in a mixing chamber so that a proper mix is maintained both prior to and during the spraying of the material.

Hydraulic pumps may be used to connect a mixing chamber for pumping mixed fire retardant material through hose to nozzle. When a proper consistency of mix is provided, a pressure of about 75-165 lbs. per square inch for example, is maintained in the hose. An air compressor is connected to hose for providing compressed air to nozzle When appropriate, compressed air is applied to nozzle at the same time the fire retardant material slurry is pumped through hose, to form an appropriate spray from the nozzle and onto structure When spraying is completed, a valve may be switched that shuts off the flow of fire retardant material through hose and in its place allows water to flow through the hose for cleaning out the hose.

The invention thus provides a method of using a fire retardant composition comprising providing an amount of fire retardant material in a dry form, such as an algae-based composition which has been dried, refined and processed into a powderized material at. The powderized material is selectively added to a liquid base to form a liquid coating material at. The liquid coating material can then be applied to a structure in a predetermined thickness before the structure may be exposed to fire at, and the coating is selectively removed from the structure after the risk of exposure to fire has passed. The materials could also be used in fire extinguishers.

As an alternative example, the fire retardant material of the invention may also be used to form building products and construction materials for use in, for example, home, commercial, industrial, automotive, aeronautic, and marine applications. These include materials panels formed from the refined algae-based composition produced as described previously, either alone or in combination with other materials in a composite form, such as containing wood, wood fiber composites, wood veneer, organic materials such as grass or bamboo, plaster, paper, open or closed cell foam, and natural or synthetic fibers. The types of construction materials may include wallboard type panels, flooring, roofing materials, siding, insulation, and paper-backed construction products. Such materials include fire barrier materials and products to protect property and control the spread of wildfires. The fire barrier material/product may be a composite having an outer layer of the fire retardant composition. The fire retardant composition may be applied before or after the fire barrier material has been placed in its protective location. For example, the refined algae-based composition may simply be formed in to the shape of a building panel that could be used alone or as a protective cover in conjunction with other building panels such as plaster wallboard, wood panel or insulation panel, or such materials could be integrated with such building materials, such as a covering on an exterior portion. Such materials could also be integrated with other building materials as a covering, such as in association with lumber.

Other building materials may be formed of or have the fire retardant materials of the invention integrated therein, such as an additive in paints using the powderized form. For example, the materials could be used as a flame retardant biomaterial in a paint, with the powder of the desiccated algae added to the paint, possibly with binders, stabilizers or fillers, and the resulting fire retardant paint mixed. The material could also be used as an insulation type material, such as a sprayed in insulation material. The refined algae material has insulation characteristics and may be sprayed into walls as a dry powder type material or sprayed onto surfaces as a slurry, similar to the examples described above, and dried in place. The fire retardant materials may include additives such as inhibitor agents to prevent molding if desired.

In another example, the fire retardant material could be used in clothing or other fiber based products. The terms below as used herein and in the accompanying claims are intended to have the following definitions. In association with such products, "Filament" means a fibrous strand of indefinite length. "Fiber" means a fibrous strand of definite length, such as a staple fiber. "Yarn" means a collection of numerous filaments or fibers which may or may not be textured, spun, twisted or combined. "Fabric" means a collection of filaments, fibers and/or yarns which form an article having structural integrity. A fabric may thus be formed by means of conventional weaving, braiding, knitting, warp-knit weft insertion, spin bonding, melt blowing techniques, or other techniques to form structurally integrated masses of filaments, fibers and/or yarns. "Textile articles" is used generically to refer to filaments, fibers, yarns and fabrics. The invention relates to forming textile articles, it being understood that such reference embraces filaments, fibers, yarns and fabrics. "Functionalized" when referring to textile articles means that such textile articles have been imparted with a desired flame retardant function which such textile article may not inherently possess without such treatment. Other functions that textile articles may be provided with by functionalizing may include, for example, anti-microbial properties, anti-static properties, and the like. "Synthetic" means that the textile article is manmade from a fiber-forming substance including polymers synthesized from chemical compounds, modified or transformed natural polymers, and minerals. Synthetic fibers are thus distinguishable from natural fibers such as cotton, wool, silk and flax. "Spinnable" is meant to refer to a liquid material which is capable of being extruded through orifices in a spinneret to form individual streams of the material which when solidified ultimately result in individual fibers of such material. Objects into which the refined algae materials may be incorporated include textiles such as those made from cotton, linen, hemp, and other natural plant fibers; wool and other animal fibers; and synthetic fibers such as acrylic, nylon, and polyester. The textile may constitute all or part of the object to be treated. The textile may be treated during production of the object or after the object is placed in use. Examples of textiles contemplated by the present invention include, but are not limited to, residential and commercial furnishings such as upholstered furniture and panels, draperies, rugs, and carpeting; linens such as bedding and pillows; mattresses and futons; and fire resistant blankets and clothing.

As it is desired with fibers in textiles, whether they are natural (e.g. cotton) or synthetic (polyester, nylon) to provide flame or fire resistance to preserve lives and property, the powderized fire retardant material may be used in association with synthetic filaments and fibers. It is also possible to combine the algae fire retardant with a fire retardant polymeric material prior to being formed into a textile article and/or to apply an appropriate functional component topically to the textile article by treating the textile article in a post-production step. The technique for imparting flame-retardant attributes to textile articles by the topical application of particulate flame-retardant materials adhered or bound to the surface of the fiber or filament materials. Most flame retardants in use today are added as fillers or contain halogens. Fillers can reduce the physical properties of the clothing, and are not bound to the fiber. Halogenated flame retardants have environmental concerns as well as release highly toxic gases during combustion. The powder could be used in the manufacture of textiles in a variety of ways. First, the dry yarns of the textiles could either be soaked in the wet ground algae paste or the wet yarns of the textiles could be tossed in the dry algae powder. The yarns may then be dried after this step. Once dried, the yarns will be coated with the algae particles with flame retardant properties imparted due to the algae coating. The yarns can then be woven or knitted into a variety of textiles having flame retardant characteristics. Chemical binders may be used to ensure that the algae particles remain attached to the textiles. The flame-retardant algae based particles may be physically associated with a textile article by chemical or physical means. For example, the algae particles may be modified so as to include one or more pendant reactive groups which serve as sites to react with, and be chemically bound or linked to, the textile article. The pendant reactive groups may be any suitable group or groups capable of reacting with functional groups present in the textile article. Examples of such reactive groups may include, for example, acrylics, methacrylics, styryls, epoxies (oxirane), isocyanates, aromatic alcohols, thiols, carboxylic acids, hydroxyls, amines, and like groups. The flame-retardant refined algae based particles may alternatively or additionally be incorporated into the small interstices of a non-woven or woven textile fabric and thereby be held physically within the fabric. Alternatively or additionally, the flame-retardant algae particles may be bonded to the textile article by means of a binder, e.g., a binder resin. Examples of binder resins that may be used satisfactorily in accordance with the present invention include acrylics, urethanes, unsaturated polyesters, vinyl esters, epoxies, phenol/formaldehyde resins, urea/formaldehyde resins and melamine/formaldehyde resins; crosslinkable acrylic resins derived from substituted acrylates such as epoxy acrylates, hydroxy acrylates, isocyanato acrylates, urethane acrylates or polyester acrylates; alkyd resins, polyester resins and acrylate resins crosslinked with melamine resins, urea resins, isocyanates, isocyanurates, carbamates or epoxy resins. Once prepared, the flame-retardant algae based particles may be applied to the surfaces of the textile article in any convenient manner. For example, if the flame-retardant algae particles are blended with a binder resin, the blend may be applied as a liquid onto the surface of the textile article by padding, dipping, spraying, roll coating or like techniques. If the textile article is in the form of a filament, fiber and/or yarn, the blend of binder resin and algae particles may be applied continuously during the production of such filaments, fibers or yarns by a roll coating applicator for example. The flame-retardant algae particles may also be combined with superabsorbent polymer (SAP) particles. The SAP particles may be comprised of SAP particles and an amount, such as between about 25 wt. % to about 500 wt. %, based on the total weight of the flame-retardant SAP particles, of an inorganic flame retardant absorbed by and physically entrained within the SAP particles. The flame-retardant SAP particles may also be sprinkled or otherwise applied during formation of a non-woven or woven textile article so that the particles will be physically captured within, and thus retained by, the fabric's interstitial spaces. The flame-retardant article of claim 1, wherein the flame-retardant SAP particles comprise a dried residue of an aqueous inorganic flame retardant solution absorbed by and physically entrained within the SAP particles.

As an example, the inorganic flame retardant may include at least one phosphorus-containing flame retardant, such as selected from the group consisting of phosphoric acid and sodium salt derivatives thereof, phosphorous acid and sodium salt derivatives thereof, ammonium orthophosphate, ammonium hypophosphate, ammonium hydrogen phosphate, ammonium dihydrogen phosphate, ammonium hypophosphite, and ammonium dihydrogen orthophosphite. Alternatively, or in addition, the inorganic flame retardant is at least one selected from the group consisting of boric acid, sodium tetraborate and hydrates thereof, sodium metaborate and hydrates thereof, and zinc borate. Any other suitable materials may be used if desired. The inorganic flame retardant may be present in an amount of between about 25 wt. % to about 200 wt. %, based on the total weight of the flame-retardant SAP particles for example. If SAP particles are used in conjunction with the algae particles, they may comprise hydrated SAP particles. The flame-retardant algae particles are designed to be present in an amount sufficient to render the textile article flame-retardant. For example, the flame-retardant algae particles may be present in an amount between about 0.1 wt. % to about 50 wt. %.

EXAMPLES

Example 1

A tissue was taped on the back of very dry piece of algae-based composition based fire resistant material having the dimensions of 5" wide by 7" tall by 3/8" thick. The flame of a propane torch (at about 3500° F.) was aimed on one spot for 20 minutes. The algae-based composition charred and turned red. The tissue on the back remained taped and unharmed for about 15 minutes. The fire resistant composition was warm to the touch on the surface where the flame was applied after less than 10 seconds, while the back of the piece was still at ambient temperature.

Example 2

Three miniature half houses (they resembled bird houses) were constructed. They all were identical: the ends 3/4" pine, front 1/2" plywood, and the roofs 1/2" plywood. All were painted with house paint, and stood 8.5" wide by 5.5" tall by 2.75" deep with a roof 5.5" tall and 8.75" long.

To the first house was added an asphalt shingle, filled it to 6" with fluffed dried algae-based composition (like blow in insulation..) held in place by hardware cloth stapled to the back of it. The algae-based composition was 6"×2.75"×7.25", just above the sidewall. The flame of a propane torch was applied. At 5 minutes the house was starting to flame. Notice the fire from the torch is pointed under the eaves like a house fire usually burns. The algae-based composition did not smoke or burn (char) .The insulation seemed to dissipate the heat and not let the roof burn. At 11 minutes, flames started to melt the tar on the shingle. 16 minutes the tar was smoking but not the insulation. At 20 minutes, there was no heat on the inside of the house (the insulation next to the hardware cloth.) The flame followed the roof line, but the algae-based composition seemed to dissipate the heat so as not to allow the roof to flame, only to char on the inside. The flame was applied for only 20 minutes.

The second house was just wood with paint. No insulation or shingle was placed on the surface. The flame of the propane torch was applied like the first house, in 4 minutes the house ignited. A hole burned through in about 45 seconds, and after 8 minutes the whole roof was burning. At 15 minutes into the burn about 3/4 of the house was burned. The flame was applied for 4.75 minutes with the torch and then the house was observed for 11.5 minutes without further application of the torch.

The third house was coated to a thickness of 3/8" with the composition of the present invention by mixing 1 cup dry shredded algae-based composition with 1 cup water and applying it to the roof. This house had a shingle, and a glass window glued on with Elmer's glue. The ambient temperature that day was 90 degrees. The flame of the propane torch as applied to the house. At 10 minutes, the measured temperature of the wood inside the house was 90 degrees, same as ambient temperature. When a second torch was added at 10 minutes, the inside wood temperature increased to 107 degrees at the 20 minutes mark. The flame was applied using 2 propane torches to the roof of the same house for 20 minutes and the temperature reached a 90 degree (same as ambient temperature) reading. The algae-based composition was wet as applied to the house to simulate how it would be if it would be if it was sprayed onto a home in the path of a fire and dried as the flame from the torch was applied. There was no smoke either from the algae-based composition or the wood. The wood was not charred, the glass window stayed glue and unbroken.

The refined algae based material of the invention may also be used in the creation of flame retardant materials, such as fire retardant mattress and furniture coverings. A yarn having the algae-based particles of material could be coated on the yarn or incorporated into the fibers to create a fire retardant layer to use in mattress and furniture coverings. This fire retardant layer could be applied underneath or on top of the external, decorative covering of the mattress or piece of furniture. In the event of fire, only the external covering could be at risk for fire damage, not the interior of the mattress or piece of furniture. Possible textiles that could be created this way include clothing, linens, mattress coverings, mattress ticking, furniture upholstery, furniture filling, carpet, window coverings and the like.

The refined algae based fire retardant may be combined with a fire retardant polymeric material, it is desired to use a non-halogenated flame retardant material such as non-halogenated flame retardant compounds manufactured from a variety of thermoplastic resins, including polyimide/nylon (PA), polycarbonate (PC), and polycarbonate/ABS (PC/ABS) blends. The material combined with a non-halogenated thermoplastic resin may also be used in other examples of the invention such as to form a coating for application to a structure for providing fire resistance to the structure, as building products such as panels, or blown in insulation type materials, or as an additive to paints or the like, or in various other applications and examples, with minimal environmental impact.

Further, the refined algae based material may be used for other applications such as the coating on wiring or cables. In such an example, the refined algae may be suitable for extrusion itself, with or without other additives, or in association with a fire retardant thermoplastic resin as set forth above, or in association with superabsorbent polymer (SAP) particles pre-loaded with moisture which are incorporated into a thermoplastic polymer and combined with the algae based material. Such materials may be extruded into desired shapes such as the outer jacket of a wire or cable, or other extruded or molded articles. The refined algae based material could be combined with other materials such as thermoplastic resins and together be ground and used in the various applications described herein. Chemical treatment of the algae based material alone or combined with other such materials is also possible, such as using a chemical flame retardant, such as non-halogenated materials.

The algae-based composition based material of the present invention could be used to protect homes, barns and buildings in paths of wild fires, for fire brakes, or for forest fires suppression, fire resistant furniture padding and bedding (cushions), couches, chairs, mattresses, window drapes, military uses, tents, ships and sub marine insulation on their pipes and walls, with explosives, as fire retardant insulation for hot and cold applications, sound barrier material.

Other applications could include as blown in insulation for old and new buildings, batted insulation for auto's, busses, RV's, buildings and homes coating, molded, extruded wall board like siding, rolled roofing (sheets replacing tar paper), roof tiles, shingles, fiber woven in protective clothing, for fireman, law enforcement, military, or for frost protector for vegetables and citrus crops. Further applications could include aero space replacement ceramic, fire suppressants for commercial kitchens, fire extinguishers, automotive firewall, muffler wrap (side Pipes), under carpeting and in carpeting, fire proof wall and sound barriers or dividers, air craft insulation and seating materials. Still further applications include as packaging, bags, grocery bags, card board boxes, skirt boards, heavy industrial fire resistant paper on wall boards, news paper, drop cloths, fine writing paper, paper rolled seed paths, cellophane, barrier and food films, and packaging films, insulation for all types of refrigeration, homes, commercial and industrial, hot water tank insulation, boiler insulation, fire/heat protective pads (welders, fire rescuers, plumbers), plant pots, fire resistant storage containers (bankers boxes), fire proof storage (pods), bakelite type plastics, fiber for asphalt and concrete, fire proof locks boxes, refractory lining, bricks, fake stone. More applications include nano scale particles for polymeric materials, as additives or fillers for paint and/or structural materials, for insulation jacketing for wire and cable, super absorbent materials, pet bedding, horses (then recycled), artificial Christmas trees, composite materials (decking, paneling. etc.), and solar heaters.

Other possible applications may include materials for use in, for example, home, commercial, industrial, automotive, aeronautic, and marine applications. These include consumer objects and goods, such as artificial Christmas trees, other molded articles, objects including paper materials, or other suitable applications.

While the invention has been illustrated and described with respect to various examples and applications, the same is to be considered as illustrative and not restrictive in character, it being understood that only illustrative embodiments thereof have been shown and described. All changes and modifications that come within the spirit of the invention described by the following claims are desired to be protected. Additional features of the invention will become apparent to those skilled in the art upon consideration of the description. Modifications may be made without departing from the spirit and scope of the invention.

I claim:

1. A process for manufacturing a fire resistant material comprising the steps of
   A. recovering Cladophora algae;
   B. mixing said algae with water to form an aqueous mixture;
   C. mixing a chlorine based solution to the mixture to kill the algae and any bacteria and to form an algae-based product;
   D. allowing the algae-based product to separate;
   E. skimming or decanting off the algae-based product;
   F. drying the skimmed or decanted off algae-based product; and
   G. recovering the dried algae-based product, wherein said dried algae-based product is a fire resistant material.

2. The process of claim 1 wherein the recovered product is compressed to remove water and then dried.

3. The process of claim 1 wherein the recovered product is dried to remove water.

4. The process of claim 1 wherein the chlorine based product is sodium hypochlorite.

5. The process of claim 1 wherein the recovered algae product is formed into a powder and remixed with water.

6. The process of claim 1 wherein the recovered algae product is formed into a powder and remixed with water and is further mixed with boric acid.

7. The process of claim 1 wherein the recovered algae product is comprised of particles having a three dimensional structure.

8. The process of claim 1 wherein the recovered algae product is comprised of particles covered by diatoms which are mono-cellular algae with an inorganic porous shell.

9. The process of claim 1 wherein the recovered algae product is formed into a powder and remixed with water and is further mixed with an organic preservative.

10. A substrate coated with the algae-based product made according to claim 1.

11. The substrate of claim 10 wherein the algae-based product is further mixed with orthoboric acid.

12. The substrate of claim 10 wherein the algae-based product is further mixed with a polymer.

13. The substrate of claim 10 wherein the algae-based product has a thickness of between about 0.01 inch and 5.0 inches thick.

14. A three-dimensional self-supporting structure made from the recovered dried algae-based product made according to claim 1.

* * * * *